(12) United States Patent
Cianci et al.

(10) Patent No.: US 12,161,534 B2
(45) Date of Patent: Dec. 10, 2024

(54) MACHINE AND A METHOD FOR PRODUCING SANITARY ARTICLES

(71) Applicant: Fameccanica.Data S.p.A., San Giovanni Teatino (IT)

(72) Inventors: Enio Giovanni Cianci, San Giovanni Teatino (IT); Diego Gualtieri, San Giovanni Teatino (IT); Matteo Antonioli, San Giovanni Teatino (IT); Anselmo Cicchitti, San Giovanni Teatino (IT)

(73) Assignee: Fameccanica.Data S.p.A., San Giovanni Teatino Chieti (IT)

( * ) Notice: Subject to any disclaimer, the term of this patent is extended or adjusted under 35 U.S.C. 154(b) by 62 days.

(21) Appl. No.: 17/717,457

(22) Filed: Apr. 11, 2022

(65) Prior Publication Data

US 2022/0323262 A1    Oct. 13, 2022

(30) Foreign Application Priority Data

Apr. 13, 2021 (EP) .................................... 21168187

(51) Int. Cl.
| | |
|---|---|
| *A61F 13/15* | (2006.01) |
| *B25J 5/02* | (2006.01) |
| *B25J 15/06* | (2006.01) |
| *B25J 19/02* | (2006.01) |

(52) U.S. Cl.
CPC .. *A61F 13/15764* (2013.01); *A61F 13/15804* (2013.01); *B25J 5/02* (2013.01); *B25J 15/0658* (2013.01); *B25J 19/023* (2013.01)

(58) Field of Classification Search
CPC .......... A61F 13/15764; A61F 13/15577; A61F 13/15804; B25J 11/00; B25J 11/0085; B25J 5/02; B25J 9/0078; B25J 9/046; B25J 9/104; B25J 9/0019; B25J 19/0065; B25J 19/023; G05B 2219/45066; G05B 2219/45098

See application file for complete search history.

(56) References Cited

U.S. PATENT DOCUMENTS

| | | | |
|---|---|---|---|
| 2018/0043538 A1* | 2/2018 | Davis | ....................... B07B 1/528 |
| 2020/0139555 A1* | 5/2020 | Paterni | ................. B25J 11/0085 |

FOREIGN PATENT DOCUMENTS

| | | |
|---|---|---|
| BR | 112019025689 A2 | 9/2020 |
| CN | 112545760 A | 3/2021 |
| EP | 0246922 A2 * | 11/1987 |
| WO | 2015167374 A1 | 11/2015 |
| WO | 2018224969 A1 | 12/2018 |

OTHER PUBLICATIONS

European Search Report dated Oct. 13, 2021. 8 pages.
Chinese Office Action dated Aug. 30, 2024.

* cited by examiner

*Primary Examiner* — Thomas M Wittenschlaeger
*Assistant Examiner* — Himchan Song
(74) *Attorney, Agent, or Firm* — RMCK Law Group PLC

(57) ABSTRACT

A machine for producing sanitary articles includes a plurality of processing stations including automated apparatus for forming sanitary articles which advance along a machine direction. The machine includes a multi-axis industrial robot arranged to automatically clean and/or inspect the automated apparatus of the processing stations. The machine has a positive impact on sustainability.

12 Claims, 3 Drawing Sheets

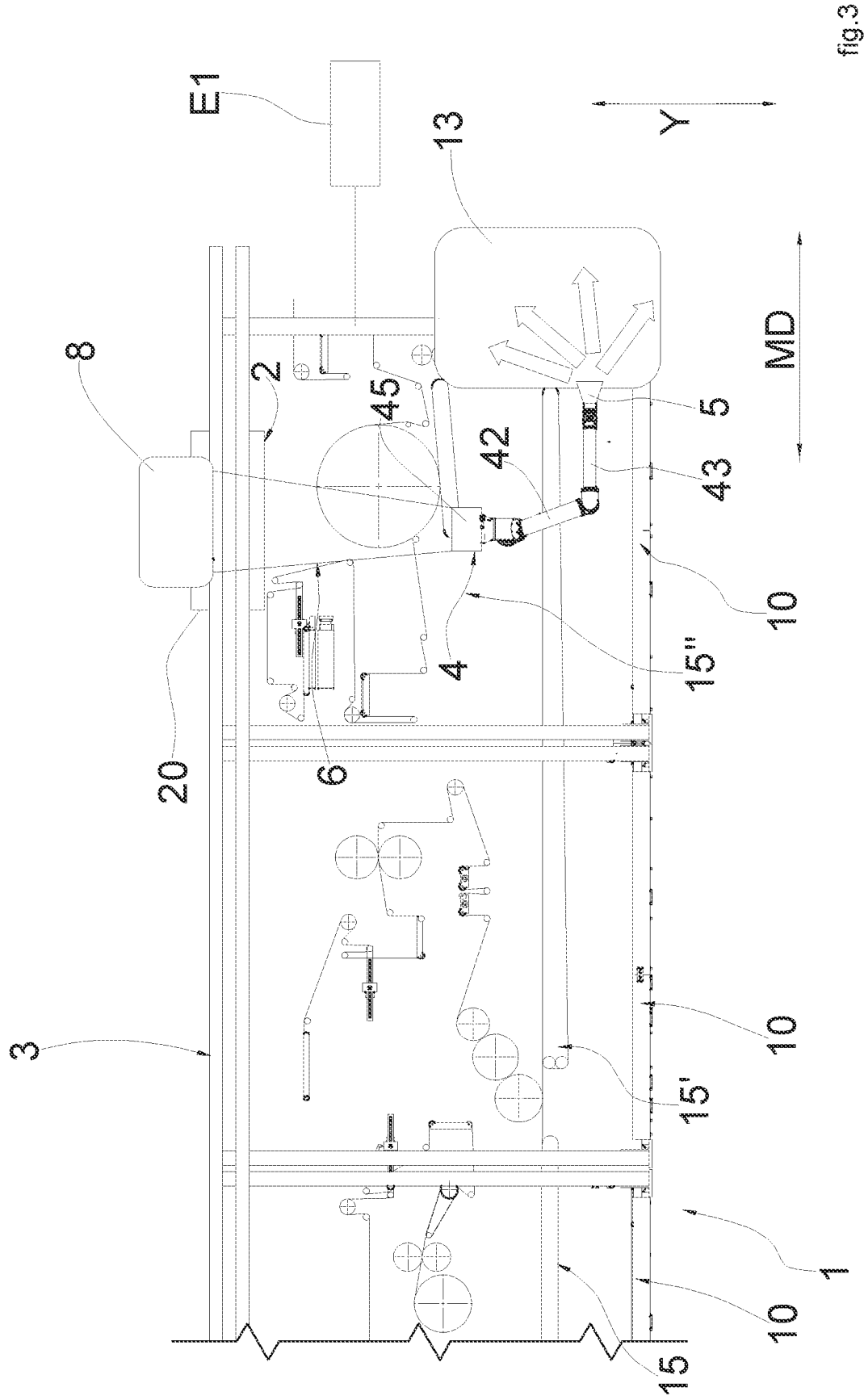

MACHINE AND A METHOD FOR PRODUCING SANITARY ARTICLES

CROSS-REFERENCE TO RELATED APPLICATION

This application claims priority to European Patent Application No. 21168187.9 filed Apr. 13, 2021. The disclosure of the above application is incorporated herein by reference in its entirety.

FIELD OF THE INVENTION

The present invention relates in general to manufacturing of sanitary articles.

More specifically, the invention relates to a machine and to a method for producing sanitary articles, envisaged for cleaning and/or inspecting automated apparatus provided for forming the sanitary articles, in a particularly efficient and cost-optimized way.

The invention has been developed with particular attention to the field of manufacturing of sanitary articles, such as sanitary pads, pantry liners, diapers, training pants, paper towels, female hygiene products, face masks, plasters, etc.

The scope of the invention is not in any case limited to this possible field of application.

DESCRIPTION OF THE PRIOR ART

Cleaning industrial parts in a factory has historically been an expensive and inefficient procedure. In this context, it is crucial to keep parts clean before beginning of the manufacturing process. Residue, oil films, particles of debris, waste material or other imperfections can all hinder downstream processes like, assembly operations, heat treatment, packaging etc.

Furthermore, in the context of the above-mentioned machines, another critical issue concerns the need to carry out several scheduled inspections of the automated parts, to ensure that the production cycle is carried out according to optimal conditions.

To date, cleaning and inspecting industrial parts in a factory is carried out manually by operators who have to be properly trained and in possession of specific certifications.

Manual cleaning and inspections involve several problems, such as risks for the operators during the interventions, need for machine shutdown which causes a reduced productivity, need for specific training and certification for the operators and difficulty to provide repeatability and high-quality of the interventions.

OBJECT AND SUMMARY OF THE INVENTION

The object of the present invention is to overcome the drawbacks and limitations of the prior art in a particularly efficient and cost-optimized way.

Another object of the present invention is to provide a machine of the type indicated above that enables the aforementioned interventions without interrupting the operation of the machine, ensuring repeatability and high-quality of the interventions.

According to the present invention, these objects are achieved by a machine having the features of claim 1.

According to another aspect, the invention relates to a method for producing sanitary articles.

The claims form an integral part of the disclosure provided here in relation to the invention.

BRIEF DESCRIPTION OF THE DRAWINGS

The present invention will now be described in detail with reference to the attached drawings, given purely by way of non-limiting example, wherein:

FIG. 3 is a schematic plan view showing further features of the machine illustrated in FIG. 1.

DETAILED DESCRIPTION

Figure 1:
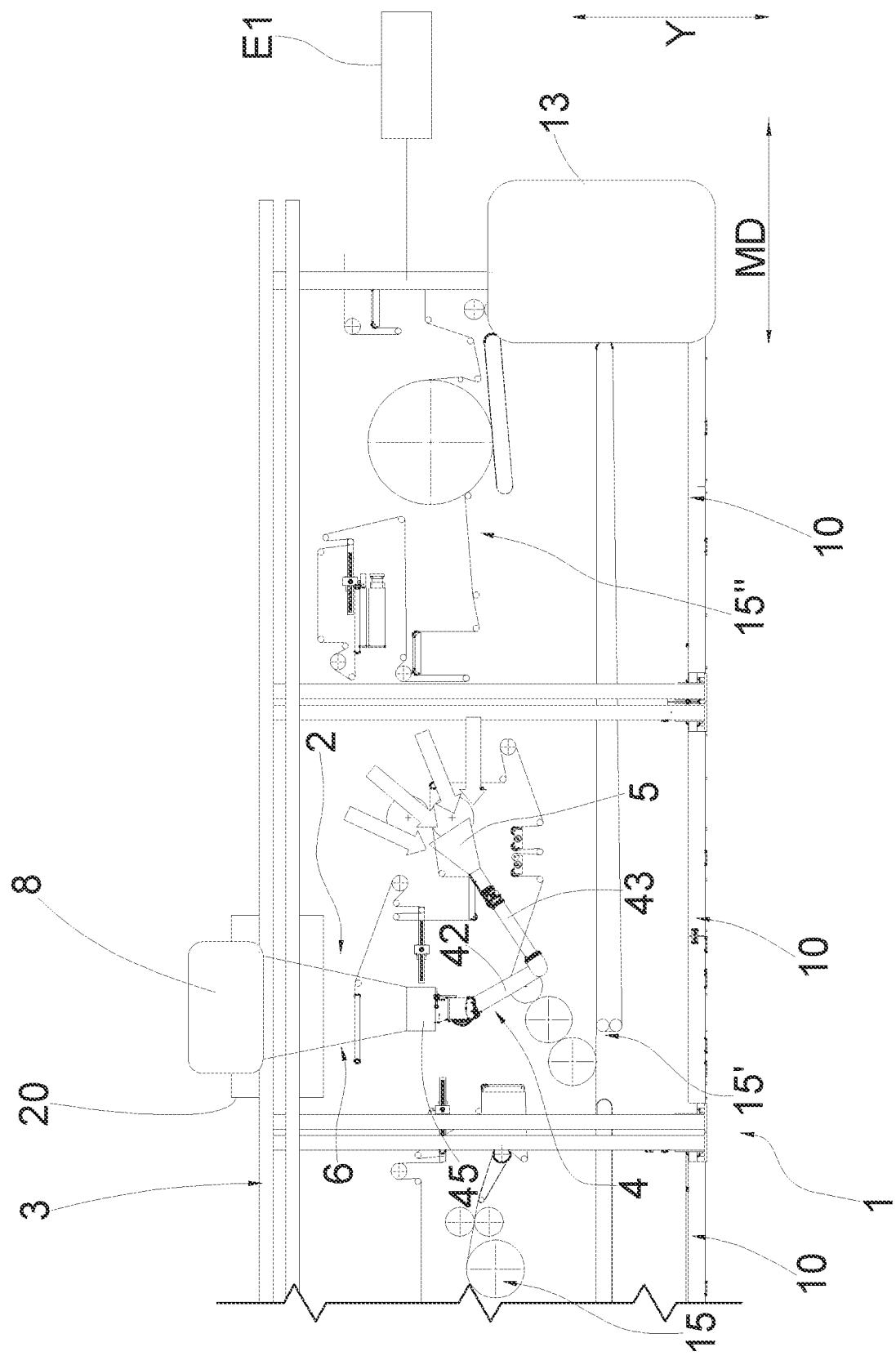
FIG. 1 is a schematic plan view illustrating a first embodiment of a machine according to the invention.

With reference to the figures, a machine for producing sanitary articles is indicated by the reference numeral 1. The machine 1 comprises a plurality of processing stations 10 arranged in series relative to each other, wherein each station 10 comprises respective automated apparatus 15,15',15" configured for carrying out specific operations for forming the sanitary articles, starting from continuous webs of raw material which advance through the stations 10 along a machine direction MD.

According to the invention, the machine 1 comprises at least one multi-axis industrial robot 4 automatically movable along the processing stations 10.

As described in detail in the following, the multi-axis industrial robot 4 is configured and driven for carrying out cleaning and/or inspecting cycles, in order to clean and/or detect operative parameters and failures of the processing stations 10 of the machine 1.

Figure 2:
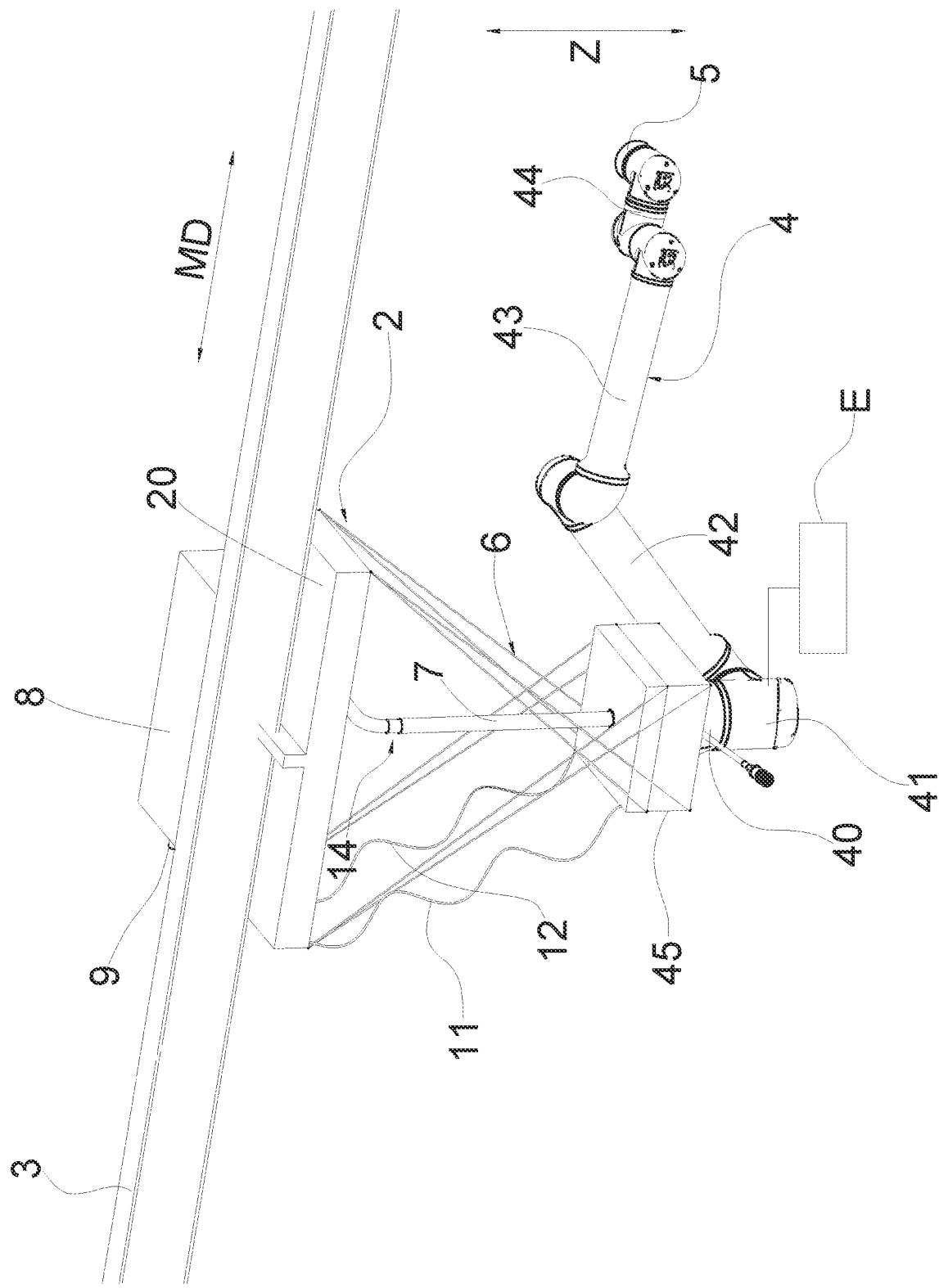
FIG. 2 is a schematic perspective view illustrating various features of a machine according to the present invention.

With reference to FIG. 2, the industrial robot 4 is movably mounted on a guide 3 by means of a handling system 2. The guide 2 extends parallel to the machine direction MD, along one side and/or above the stations 10, so as to not interfere with the automated parts of the stations 10.

In a possible embodiment, the handling system 2 comprises a carriage 20 slidably mounted on the guide 3 along a machine direction MD, so as to enable the robot 4 to easily reach all the equipment located in each station 10. Preferably, the machine 1 comprises at least one auxiliary vertical guide orthogonal to the guide 3 provided for vertically sliding the carriage 20. The auxiliary vertical guide may be connected with the guide 3 extending along the machine direction MD, so as to define a single path for the carriage 20 which can travel along machine and vertical directions. In a possible embodiment, one end of the vertical guide may be provided on the ground surface of the machine 1. In this connection, the robot 4 can be positioned on the carriage 20 which comprises drive wheels for switching from the vertical guide to the ground surface and automatically moving over the ground. In one or more embodiments, the machine 1 comprises a plurality of parallel vertical guides connected to the guide 3 spaced along the machine direction MD, wherein each vertical guide is associated to a respective station 10. Due to this feature, the carriage 20 may be driven vertically along each station 10.

According to the embodiment illustrated in FIG. 2, the robot 4 is an anthropomorphic robot having a base 40 and a column 41, which is rotatably mounted on the base 40 about a first axis directed vertically. The robot 4 has an arm 42 mounted on the column 41 pivoted about a second axis directed horizontally. The reference 43 designates a forearm mounted on the arm 42. The forearm 43 is pivoted about a third axis, which is also directed horizontally; the forearm 43 also has the possibility of rotating about its longitudinal axis; the forearm 43 of the robot 4 is provided with a wrist 44 at its end opposite to the arm 42, which is mounted with the possibility to rotate about two mutually orthogonal axes. All the axes of the robot 4 can be controlled by a respective electric motor. The electric motors of the robot 4 are controlled by an electronic control unit E (schematically illustrated in FIG. 2). Therefore, the wrist 44 of the robot 4 is connected to the base 41 of the robot 4 by means of a chain of robot elements 41, 42, 43, that are mutually pivoted about respective robot axes. A flange is provided at distal end of the wrist 44, for attachment of a tool carried by the robot. Still regarding to the preferred embodiment, the robot comprises a stabilizer 45 associated with the base 40 of the robot 4, which is schematically illustrated in FIG. 2.

Naturally, as an alternative to what is illustrated in FIG. 2, the robot 4 can be made according to other arrangements such as for example a robot including a pair of wrists.

As previously indicated, the industrial robot 4 is movably mounted along the stations 10 by means of a handling system 2. In one or more embodiments, the handling system 2 comprises a cable-driven robot 6 configured for moving the industrial robot 4 along the stations 10. With the expression "cable-driven robot" is intended a type of automated cable-driven unit in which flexible cables are used as actuators. One end of each cable is reeled around a rotor twisted by a motor and the other end is connected to an end-effector. In the case of the invention, one end of each cable is connected to the carriage 20 and the other end is connected to the industrial robot 4, in particular to a vertex of the base 40. It is to be noted that the cable-driven robot 6 is schematically illustrated in the drawings and the actuators are not illustrated, since the person skilled in the art well knows how to provide a functioning arrangement.

Preferably, the cable-driven robot 6 is connected so as to enable the industrial robot 4 to move with six degrees of freedom, consisting of three in translation and three in orientation according to axes MD, Y, Z.

In operation, the industrial robot 4 is supported to the carriage 20 by cables of the cable-driven robot 6 which moves integrally with the carriage 2 along the machine direction MD. As previously indicated, by driving the cable-driven robot 6, the industrial robot 4 is able to move with six degrees of freedom, consisting of three in translation and three in orientation according to axes MD, Y, Z.

As previously indicated, the multi-axis industrial robot 4 is configured and driven for carrying out cleaning and/or inspecting cycles, in order to clean and/or detect operative status of the processing stations 10 of the machine 1.

In a possible embodiment, the industrial robot 4 comprises an end-effector 5 connected to the wrist 44, arranged to automatically clean the automated apparatus 15,15',15" of the stations 10. In this connection, the industrial robot 4 is configured for automatically moving along the processing stations 10 and vacuum waste material resulting from the production of the sanitary articles, without interfering with the operation of the automated apparatus 15,15',15". Preferably, the machine 1 comprises a suction device connected to the end-effector 5 of the robot 4 so as to vacuum the waste material. The suction device may comprise an intake port and a fan driven by an electric motor, in order to vacuum dirt particles and debris resulting from the production of the sanitary articles.

Preferably, the machine 1 comprises a conveying and collection system 14 associated with the robot 4, configured to store the suctioned material. According to the embodiment illustrated FIG. 2, the conveying and collection system 14 comprises a duct 7 connected to a collection bag 8, provided for the accumulation of the suctioned material. In a possible embodiment, the duct 7 is a corrugated flexible pipe connected to the collection bag 8 provided with an air filter 9. The collection bag 8 is mounted on the carriage 20 and—during operation—moves integrally with the carriage 20. In operation, the industrial robot 4 may be driven for sucking the waste material accumulated in the stations 10 (FIG. 1).

In a possible embodiment, the machine 1 may comprise a blower device connected to the end-effector 5 of the robot 4, provided for blowing-off the suctioned material. In that case, the machine 1 comprises a dust bag 13 provided for collecting the vacuum waste material, in which the industrial robot 4 can blows the waste material. Preferably, the dust bag 13 is fixed at a specific station 10 of the machine 1. In operation, the industrial robot 4 may be driven for blowing-off the sucked waste material into the dust bag 13 (FIG. 3).

In a possible embodiment, the machine 1 is configured for driving the industrial robot 4 so as to carry out a first cleaning step wherein the suction device vacuum said material along the stations 10 and a second cleaning step wherein the blower device blows the sucked material into the dust bag 13. Once a number of cleaning operations are completed, the dust bag 13 can be emptied for enabling further cleaning operations.

In a possible embodiment, the industrial robot 4 may comprise a UV light, provided for emitting infrared heating.

In a possible embodiment, the industrial robot 4 may comprise a steam cleaning device connected to the end-effector 5, provided for releasing steam so as to quickly dry and sanitize the stations 10 and the automated apparatus 15,15',15".

Due to the features indicated above, in operation, the industrial robot 4 automatically moves along the processing stations 10, in order to clean the stations 10 and the relative automated apparatus 15,15',15" (e.g. vacuum waste material resulting from the production of the sanitary articles). In operation the cable-driven robot 6 provides supporting of the industrial robot 4 above the stations 10, and the industrial robot 4 can perform cleaning operations of the stations 10, during movement along different directions and without interfering with automated apparatus 15,15',15" and/or operators of the stations 10. Therefore, the machine 1 provides efficient cleaning of the stations 10 without interrupting the production flow of the articles, thus maximizing the production efficiency.

In a possible embodiment, the industrial robot 4 comprises an end-effector 5 connected to the wrist 44, arranged to automatically inspect the automated apparatus 15,15',15" of the processing stations 10. In this connection, the industrial robot 4 is configured for automatically moving along the processing stations 10 and detecting operative parameters and/or failures of the automated apparatus 15,15',15" of the stations 10, without interfering with the operation of the automated apparatus 15,15',15".

Preferably, the machine 1 comprises a set of sensors comprising at least one camera for enabling the robot 4 to carry out said automated inspection. The camera may be arranged on-board of the robot 4, so as to provide imaging-based automatic inspection and process control. It is to be noted that the acquisition of the images may be carried out by using cameras, lenses, and lighting configured to provide the data required by subsequent processing, also in the case of the cleaning process.

In this connection, the machine 1 comprises a main electronic control unit E1 configured to drive the entire cleaning and/or inspecting process and a memory associated to the main electronic control unit E1, configured to store different cleaning and/or inspecting cycles information, such as map of the processing stations 10 and information related to the automated apparatus 15,15',15". The main electronic control unit E1 is electronically connected to the electronic control unit E which drives the electric motors of the industrial robot 4. Power and signal transmission are provided with electrical wirings 11,12. The main electronic control unit E1 is further configured for driving the carriage 20 and the cable-driven robot 6.

As previously indicated, the acquisition of the images may be carried out for providing the data required by subsequent processing, in order to carry out cleaning and/or inspection cycles. The main electronic control unit E1 may be configured for receiving the parameters detected by the aforementioned sensors and to process said parameters, so as to communicate to the industrial robot 4—in real time with the operation of the automated apparatus 15,15',15" of the stations 10—specific cleaning and/or inspection cycle information, enabling the industrial robot 4 to automatically navigate through the stations 10 and to carry out the cleaning/inspection process, simultaneously with the production cycle.

In one or more embodiments, the sensors comprise an infrared sensor, a photocell sensor and a camera configured to carry out remote monitoring of the cleaning/inspection operations and/or live troubleshooting steps and/or detection of noise and temperature of the automated apparatus 15,15', 15" of the stations 10.

In one or more embodiments, a predetermined cleaning/inspection cycle can be programmed preliminarily to the execution of the operations. An operator can choose a specific cycle among a number of cycles stored in the memory associated with the main electronic control unit E1. By way of non-limiting example, a specific cycle can be programmed for cleaning/inspecting only some of the processing stations 10 or some of the automated apparatus 15,15',15" located in a specific station 10.

In a possible embodiment, the machine 1 is configured for carrying out a predetermined operative cycle in which, at predetermined intervals, the industrial robot 4 automatically moves along the machine direction MD, identifies a specific processing station 10, performs power supply connections and proceeds with cleaning and/or inspecting the automated apparatus 15,15',15" of said specific processing station 1.

As it is evident from the above description, the present invention provides a machine 1 for producing sanitary articles capable to automatically clean and/or inspect automated apparatus 15,15',15" operative in a plurality of processing stations 10, avoiding risks for the operators during the interventions, need for machine shutdown causing a reduction in productivity, need for specific training and certification for the operators and also providing repeatability and high-quality of the cleaning/inspections.

Furthermore, the invention allows providing of the aforementioned advantages with an energy-efficient procedure, which has a positive impact on sustainability.

Of course, without prejudice to the principle of the invention, the details of construction and the embodiments can be widely varied with respect to those described and illustrated, without thereby departing from the scope of the invention as defined by the claims that follow.

The invention claimed is:

1. A machine for producing sanitary articles, comprising:
    a plurality of processing stations comprising automated apparatus configured for forming sanitary articles starting from continuous webs of raw material which advance along a machine direction,
    a guide that is parallel to the machine direction and extends longitudinally along the machine direction along the plurality of processing stations, the guide being fixed to the machine,
    a handling system movably mounted on the guide and configured to move relative to the guide along the plurality of processing stations,
    a multi-axis industrial robot automatically movable along said plurality of processing stations by means of said handling system,
    said multi-axis industrial robot comprising an end-effector arranged to automatically clean and/or inspect the automated apparatus of the plurality of processing stations,
    a main electronic control unit configured to drive a cleaning and/or inspecting process carried out by the multi-axis industrial robot in real time with an operation of the automated apparatus for producing the sanitary articles,
    wherein, in operation, said multi-axis industrial robot is driven for automatically moving along the plurality of processing stations, cleaning and/or detecting operative parameters and failures of the automated apparatus of the plurality of processing stations by means of said end effector, simultaneously with the operation of the automated apparatus,
    wherein said handling system comprises:
        a carriage slidably mounted on said guide, and
        a cable-driven robot associated with the carriage, configured for moving said multi-axis industrial robot with six degrees of freedom, consisting of three in translation and three in orientation according to three axes.

2. The machine of claim 1, comprising a set of sensors including at least one camera for enabling automated cleaning and/or inspection operations of the automated apparatus.

3. The machine of claim 1, wherein said multi-axis industrial robot comprises a suction device connected to said end-effector so as to vacuum waste material resulting from production of the sanitary articles.

4. The machine of claim 3, comprising a conveying and collection system associated with the multi-axis industrial robot, configured to store the waste material, wherein said conveying and collection system comprises a duct connected to a collection bag provided for the accumulation of the waste material.

5. The machine of claim 4, wherein said collection bag is mounted on said carriage and moves integrally with said carriage.

6. The machine of claim 3, wherein said multi-axis industrial robot comprises a blower device connected to said end-effector, so as to blow-off the vacuumed waste material.

7. The machine of claim 6, wherein said machine is configured for driving said multi-axis industrial robot so as to carry out a first cleaning step wherein the suction device vacuums said waste material along the processing stations and a second cleaning step wherein the blower device blows into a dust bag the vacuumed waste material.

8. The machine of claim 1, wherein the main electronic control unit is configured for driving the entire cleaning and/or inspecting process, and wherein a memory is associated to said main electronic control unit configured to store different cleaning and/or inspecting cycles information.

9. The machine of claim 8, wherein during a production cycle of said sanitary articles, the multi-axis industrial robot is configured for carrying out a predetermined operative cycle in which, at predetermined intervals, the multi-axis industrial robot is configured for automatically moving along the machine direction, identifying a specific processing station, performing power supply connections, and proceeding with cleaning and/or inspecting the automated apparatus of said specific processing station.

10. The machine of claim 1, wherein said multi-axis industrial robot is an anthropomorphic robot comprising:
   a base and a column which is rotatably mounted on the base about a first axis directed vertically,
   an arm pivotally mounted on the column about a second axis directed horizontally,
   a forearm pivotally mounted on the arm about a third axis directed horizontally, and
   a wrist mounted at a terminal end of the forearm, connected to said end effector.

11. A method for producing sanitary articles using the machine according to claim 1, the method including:
   providing the plurality of processing stations comprising automated apparatus for forming said sanitary articles starting from continuous webs of raw material which advance along the machine direction,
   providing the handling system movably mounted on the guide parallel to the machine direction extending along the plurality of processing stations,
   providing at least one multi-axis industrial robot automatically movable along the plurality of processing stations, said multi-axis industrial robot comprising the end-effector arranged to automatically clean and/or inspect said automated apparatus, and
   automatically moving said multi-axis industrial robot along the plurality of processing stations, cleaning and/or detecting operative parameters and failures of the automated apparatus of the plurality of processing stations by means of said end effector, simultaneously with an operation of the automated apparatus for producing the sanitary articles.

12. The method of claim 11, comprising carrying out a predetermined operative cycle in which, at predetermined intervals, the multi-axis industrial robot is configured for automatically moving along the machine direction, identifying a specific processing station, performing power supply connections, and proceeding with cleaning and/or inspecting the automated apparatus of said specific processing station.

* * * * *